United States Patent [19]

Smith

[11] Patent Number: 5,464,436
[45] Date of Patent: Nov. 7, 1995

[54] METHOD OF PERFORMING LASER THERAPY

[75] Inventor: Chadwick F. Smith, Rolling Hills, Calif.

[73] Assignee: LaserMedics, Inc., Stafford, Tex.

[21] Appl. No.: 233,426

[22] Filed: Apr. 28, 1994

[51] Int. Cl.⁶ ...................................................... A61N 5/00
[52] U.S. Cl. ...................................... 607/89; 606/3; 606/9; 606/13
[58] Field of Search ............................. 607/88–90; 606/3, 606/9, 13

[56] References Cited

U.S. PATENT DOCUMENTS

| | | |
|---|---|---|
| 4,612,604 | 9/1986 | Schlvter . |
| 4,686,979 | 8/1987 | Gruen et al. . |
| 4,686,986 | 8/1987 | Fenyo et al. ............................. 607/90 |
| 4,836,203 | 6/1989 | Müller et al. . |
| 4,930,504 | 6/1990 | Diamantopoulos et al. . |
| 4,973,848 | 11/1990 | Kolobanov et al. . |
| 4,989,605 | 2/1991 | Rossen . |
| 5,011,483 | 4/1991 | Sleister . |
| 5,029,581 | 7/1991 | Kaga et al. . |
| 5,050,597 | 9/1991 | Daikuzono . |
| 5,062,842 | 11/1991 | Tiffany . |
| 5,071,416 | 12/1991 | Heller et al. . |
| 5,123,902 | 6/1992 | Müller et al. . |
| 5,130,997 | 7/1992 | Ortiz et al. . |
| 5,150,704 | 9/1992 | Tatebayashi et al. . |
| 5,161,526 | 11/1992 | Hellwing et al. . |
| 5,217,455 | 6/1993 | Tan . |
| 5,222,953 | 6/1993 | Dowlatshahi . |
| 5,231,984 | 8/1993 | Santana-Blank . |
| 5,246,436 | 9/1993 | Rowe . |
| 5,312,395 | 5/1994 | Tan et al. ............................. 606/3 X |
| 5,344,434 | 9/1994 | Talmore ............................. 607/88 |

Primary Examiner—Angela D. Sykes
Attorney, Agent, or Firm—Whitham, Curtis, Whitham & McGinn

[57] ABSTRACT

A method of treating a patient, includes providing a laser source for emitting a laser light, diagnosing an afflicted area of the patient, delivering the laser light to the afflicted area for at least one treatment cycle, the laser source being operable on the afflicted area at a level of 1 Joule/cm² per treatment cycle, monitoring the afflicted area after the treatment cycle has been completed, and repeating the steps of diagnosing and delivering the laser light to the afflicted area based on the monitoring step. Each treatment cycle preferably has a duration of 33 seconds and the wavelength of the laser light is preferably between a range of 800–870 nm, and more preferably is substantially 830 nm.

20 Claims, 5 Drawing Sheets

| J. per. treatment point | Skin/ mucosa | Subcuta- neous tissue | Muscles | Tendons | Vessels | Nerves | Bones | Joints |
|---|---|---|---|---|---|---|---|---|
| Inflammation | 0.5–1 | 1–2 | 2–4 | 1–4 | 1–2 | 1–2 | 3–5 | 2–4 |
| Oedema | 1–2 | 1 | 2 | 2 | 1 | 1–4 | – | 3–5 |
| Haematoma | 0.5–1 | 1 | 2 | – | 1–2 | – | – | 3–5 |
| Contusions | 1 | 1–2 | 2–4 | 2–4 | 1–2 | 2–4 | 3–7 | 3–7 |
| Ulcers | 0.5–1 | 1–2 | 2–4 | 2–4 | – | – | – | – |
| Strains/Sprains | – | – | 2–4 | 2–4 | – | 2–4 | – | 2–6 |
| Ruptures | 0.5–1 | 0.5–1.5 | 2–4 | 2–4 | – | 1–2 | – | 2–6 |
| Contractures | 1–1.5 | 1–2 | 4–7 | 5–10 | – | – | – | – |
| Fractures/Fissures | – | – | – | – | – | – | 2–6 | – |
| Avulsions | – | – | 2–4 | 3–4 | – | – | – | 4–6 |
| Dislocations | – | – | – | – | – | – | – | 4–6 |
| Necrosis/Gangrene | 0.5–1 | 1–2 | 2–4 | 2–4 | 1–2 | 1–2 | – | – |
| Atrophy | 1 | 2 | 4–7 | – | – | 3–5 | – | – |
| Paresis/Paralysis | – | – | 2–4 | – | – | 1–4 | – | – |
| Arthritis | – | – | – | – | – | – | – | 1–10 |
| Postoperative | 0.5–1 | 1–2 | 2–4 | 2–4 | 1–2 | 1–4 | 2–6 | 2–4 |
| Using Acupuncture points | 3/4 | – | – | – | – | 3/4 | – | – |

FIG.5

| | Subcutaneous tissue, Mucosa | Muscles | Tendons | Nerves | Vessels | Bones | Joints |
|---|---|---|---|---|---|---|---|
| Inflammation | * | * | * | * | * | * | * |
| Oedema | * | * | * | * | * | — | * |
| Necrosis/Gangrene | * | * | * | * | * | — | * |
| Atrophy | * | * | — | * | — | — | — |
| Contusions | * | * | * | * | * | * | * |
| Haematoma | * | * | — | — | * | — | * |
| Strains/Sprains | — | * | * | * | — | — | * |
| Ruptures | * | * | * | * | — | — | * |
| Dislocations | — | — | — | — | — | — | * |
| Contractures | * | * | * | — | — | — | — |
| Fractures/Fissures | — | * | — | * | — | * | — |
| Paresis/Paralysis | — | — | — | * | — | — | — |

FIG. 6

* = respond to LLLT

METHOD OF PERFORMING LASER THERAPY

DESCRIPTION

BACKGROUND OF THE INVENTION

1. Field of the Invention

The present invention generally relates to a method of performing therapy on a patient for symptomatic relief and management of pain and adjunctive treatment in the management of traumatic acute pain. More particularly, the invention relates to a method of performing low level laser therapy (LLLT) on a patient.

2. Description of the Related Art

Biological systems require energy for continued metabolism, function and repair. Normal cellular metabolism provides chemical energy and homeostatic heat for nominal biological system function. When injury to a biological system (e.g., organs, tissues, cells) occurs, usual metabolic systems may not be able to maintain homeostatic energy requirements.

Biological systems consist of enzymes and membranes which selectively allow certain ions, proteins, carbohydrates, etc., to function and move in and out of the cells. Several mechanisms, including receptor mediated movement, allow these enzyme systems and membranes to perform their selective function. Injury to these enzyme and membrane systems causes membrane de-stabilization and loss of selective function. This membrane injury can result in swelling and edema.

In many cases the addition of energy to these enzyme and membrane systems can cause re-stabilization and return of other normal functions of the organ, tissue, or cell containing the enzyme/membrane system.

Surface heat has long been used in medicine to stimulate blood flow to injured tissue. Raising tissue temperature also stimulates the immune system which in turn enhances repair of damaged tissue. Surface heat has the disadvantages of superficial tissue damage and a long application time to deliver heat (energy) to deep tissues. Laser energy can be delivered as photons to tissues below the skin surface without causing superficial heating adverse effects. The use of lasers is useful with physical therapy practice within a specific portion of the electromagnetic spectrum.

Administering transcutaneous energy in the form of light and/or electrical current is generally known to be particularly used to alleviate certain types of pain. Such treatments are typically compared to acupuncture in terms of application and results. It is also generally known that the body will react favorably to certain preselected frequencies.

However, the conventional systems utilize thermal laser light which has certain destructive properties upon penetration and absorption. Virtually all light has some penetration. However, the light is quickly absorbed by the outermost skin layers. Thermal or high energy (>1 W) laser light can penetrate the skin layers (for cutting) but can also destroy tissues, thereby having a deleterious effect on the treatment schedule. Thus, while treatment with lasers can result in a site specific and condition specific response depending on the extent and type of enzyme/membrane/tissue injury, the use of deep penetrating thermal laser light may cause injury to the patient, even though the laser energy may serve as a signal and/or energy source for the repair process to proceed.

In view of the foregoing, hitherto the invention, there has been no method or system for reaching deeply into tissue without harming the surrounding tissues and thus there have been no methods or systems for optimizing the treatment of a patient using LLLT.

SUMMARY OF THE INVENTION

It is therefore an object of the present invention to provide a therapeutic method which can reach deep into tissues yet not harm the tissues, as in the conventional systems.

A unique and unobvious aspect of the invention is selection and utilization of a non-thermal wavelength of 830nm which can reach deep into tissues and yet not have the destructive effect of hot lasers. This powerful therapeutic effect is provided by the specific photodynamic properties inherent to low energy lasers.

The invention utilizes a wavelength precisely within the light spectrum documented as having an optimum biological effect on tissue and having maximum penetration. The method of the invention utilizes precise and accurate dosimetry.

In a first aspect of the invention, the method of treating a patient according to the invention includes the steps of providing a laser source; diagnosing an afflicted area of the patient; delivering a low level laser light to the afflicted area for at least one treatment cycle, the laser being operable on the afflicted area at a level of 1 Joule/cm$^2$ per treatment cycle; monitoring the afflicted area after the treatment cycle has been completed; and repeating the steps of diagnosing and delivering the low level laser light to the afflicted area based on the monitoring step. Each of the treatment cycles preferably has a duration of 33 seconds.

With the invention, a therapeutic method is provided in which laser therapy can reach deep into tissues and yet not harm the tissues, as in the conventional systems. More specifically, the inventive method involves selection and utilization of a non-thermal wavelength of substantially 830 nm, for a predetermined time period depending on the tissues to be treated, which can reach deep into tissues and yet will not have the destructive effect of "hot" (high energy) lasers. This powerful therapeutic effect is provided by the specific photodynamic properties inherent to low energy lasers.

BRIEF DESCRIPTION OF THE DRAWINGS

The foregoing and other objects, aspects and advantages will be better understood from the following detailed description of a preferred embodiment of the invention with reference to the drawings, in which:

FIG. 5 illustrates a Table used as a guide for treatment dosages with the handheld tool of FIG. 1; and FIG. 6 illustrates a Table which indicates conditions which respond to LLLT for various tissue lesions with examples of individual types of tissue.

DETAILED DESCRIPTION OF A PREFERRED EMBODIMENT OF THE INVENTION

Figure 1:
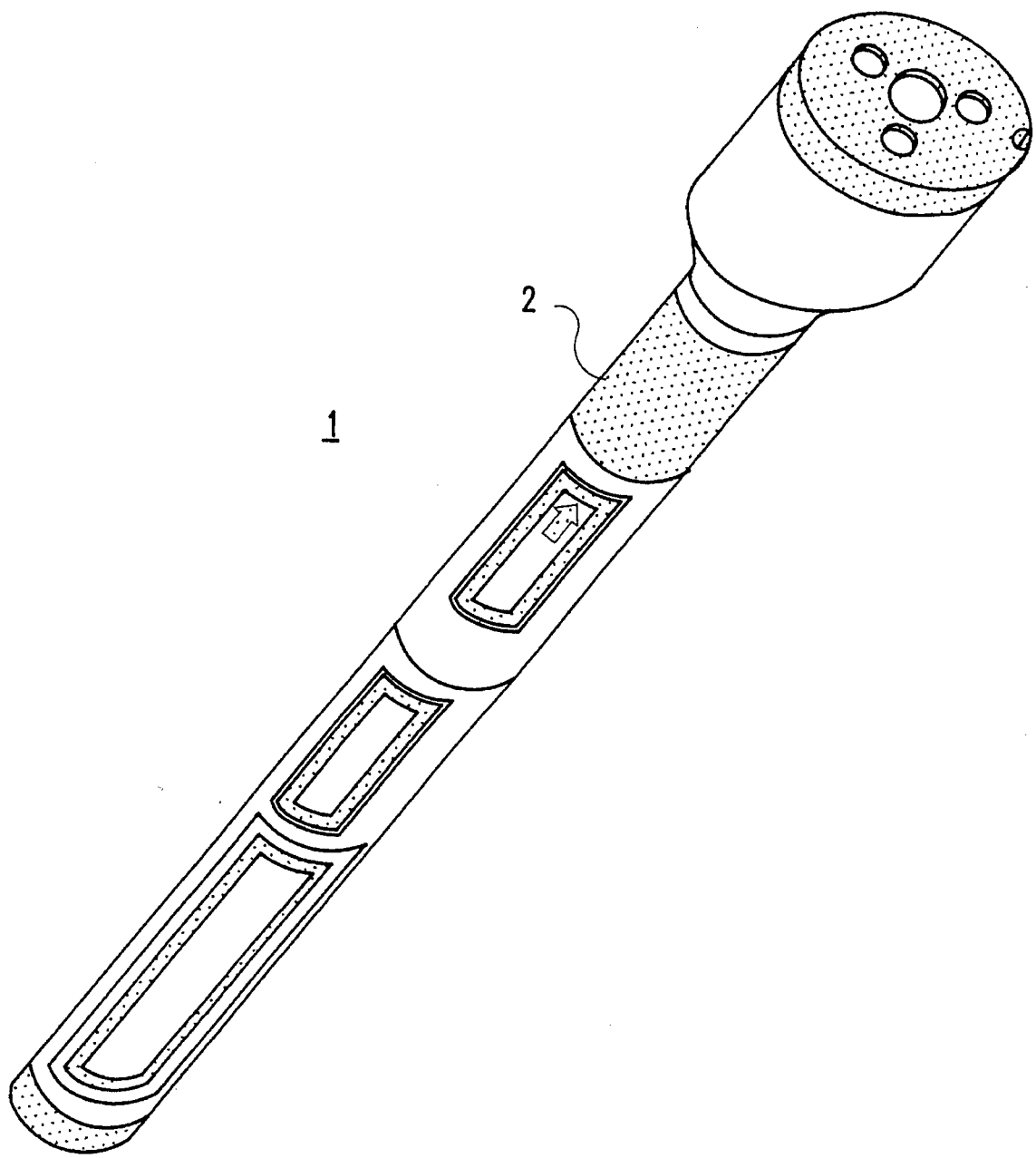
FIG. 1 is a perspective view of a handheld laser tool for performing low level laser therapy on a patient.

Referring now to the drawings, and more particularly to FIG. 1, there is shown an apparatus 1 for performing low level laser therapy according to the invention. The apparatus is a handheld laser tool commercially available, for example, from LaserMedics of Stafford, Tex. under the tradename of "LaserMedics VMD 830" or a "MicroLight 830". The laser tool 1 can be of a single or a multiple-diode model (as shown in FIG. 1) depending upon the treatment protocol to be performed. FIG. 1 illustrates a mtiltiple-diode (e.g., GaAlAs laser diodes) model for issuing a laser light having wavelength of 830 nanometers. The laser tool is battery-operated, and produces a laser wavelength of between 800–870 nm., (preferably set for 830 nm) and a laser power of 30–70 mW continuous wave (cw), (preferably set for 70 mW). The laser energy delivered is 1 Joule with the treatment cycle duration preferably being 33 seconds. The laser tool has a lens system such that the beam diameter can be formed to be approximately 3 mm$^2$ (e.g., a 1 mm×3 mm rectangle). The dimensions of the tool are approximately 2.1 cm. in diameter by 20.3 cm. long and weighs approximately 125 grams. The total laser energy deliverable from the fully charged battery is approximately more than 100 Joules. The size and shape of the laser tool 1 can be modified depending upon the patient (e.g., human or animal) to be treated.

Figure 2:
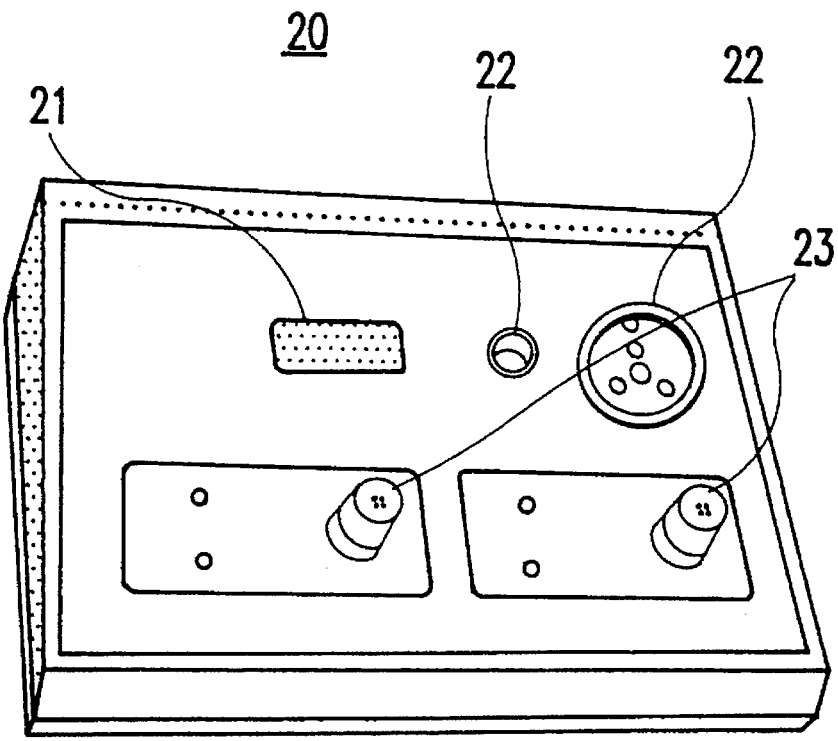
FIG. 2 illustrates an example of a recharger for charging the handheld tool shown in FIG. 1.

As shown in FIG. 2, a recharger 20 is used for receiving and charging batteries of the laser tool 1. The recharger is coupled to an ordinary AC outlet (e.g., 120V/60A) via a cord (not illustrated). The laser tool can be inserted into the recharger shown in FIG. 2 and charged as required, or, alternatively, the recharger can charge rechargeable batteries which are insertable into the laser tool. A rechargeable battery is connected to the laser tool 1 by carefully threading the battery onto a threaded end of the laser tool.

The recharger has a light emitting diode meter 21 thereon to measure the laser energy output of either the single or multiple diode models. There are a plurality of probe sensors 22 on the recharger located to the right of the LED meter, one for each of the types of laser tools (e.g., single or multiple diode models).

To test the power output of the laser unit, the appropriate probe sensor is located on the recharger. The head of the laser unit is placed into the appropriate probe sensor port and gently holds the laser unit steady during testing. A laser annular switch 2 (shown in FIG. 1) is activated by gently squeezing this surface. This also activates an audible sound which preferably continues for 33 seconds. At the completion of 33 seconds, there is a short, continuous, and audible tone and the meter reading is noted. The output is measured in milliwatts.

For a single diode model, the meter should read 70 mW (+/−3 mW). For the multiple diode model, the meter should read approximately 90 mW (+/−5 mW). If the reading is within the above levels, the unit is ready for use.

The batteries can also be charged by the recharger by removing them from the laser tool and threading them to one of the battery mounts 23 on the recharger until finger tight. Illuminated light to the left of the battery mount indicates a status of the battery charging. For example, the "CHARGE" indicator illuminates when the battery is being charged. The "READY" indicator indicates when the battery is charged to about 50% of full capacity. Preferably, the automatic laser activation cycle is 33 seconds. During the 33-second interval, an acoustic beep is produced at half-second intervals to indicate that the unit is operating.

One 33-second programmed cycle administers one Joule of energy according to the following formula:

Energy (Joules)=Mean Power (W)×Time (sec.)

Energy=0.03 W×33 Seconds=~0.99 Joules

Figure 3:
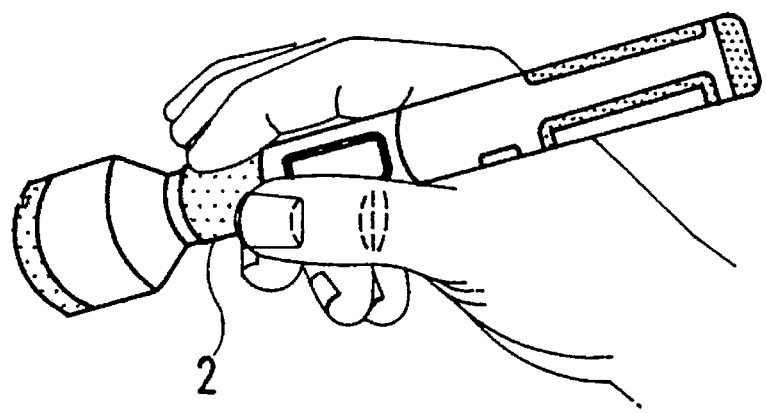
FIG. 3 illustrates the handheld laser tool of FIG. 1 being held by an operator.

As mentioned above, the laser tool 1 is activated by the annular switch 2. Activation occurs first by depressing the switch by gently squeezing anywhere on the surface as shown in FIG. 3, which illustrates the laser tool being hand-held by an operator. Once the laser is activated, no further pressure is required on the annular switch to continue the 33-second cycle. The laser unit remains activated for one 33-second cycle or until the annular switch is lightly depressed again.

In the embodiment of FIG. 1, a plurality (e.g., three) of diodes are provided similar to that discussed above with the exception of laser power and laser energy delivered (as well as the dimensional differences). Laser power is 3×30 mW continuous waves (cw) and laser energy delivered per treatment cycle is 3×1 Joule. As mentioned above; however, a single diode model may be employed.

Figure 4:
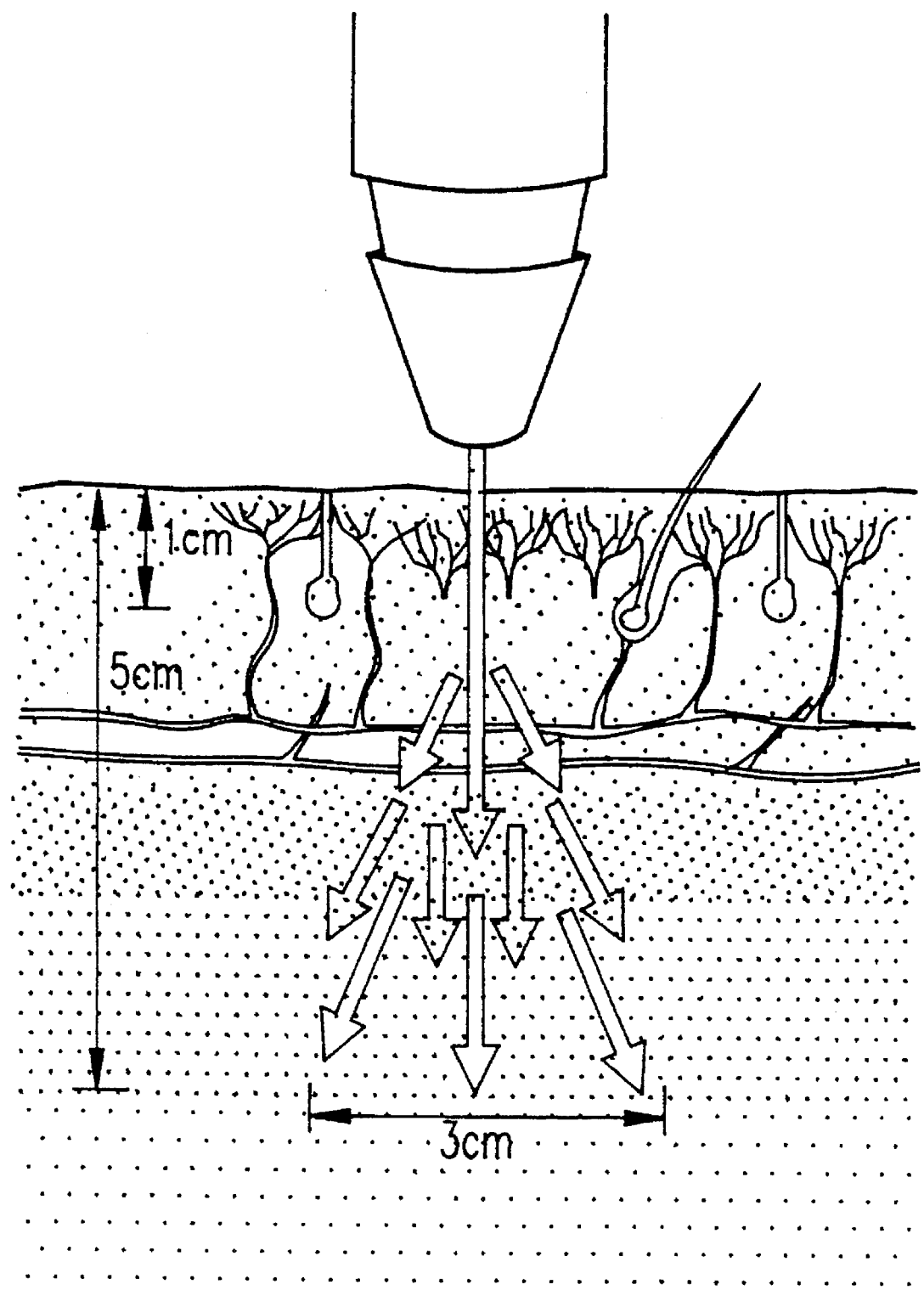
FIG. 4 illustrates an example of a patient's tissues being treated with the handheld tool of FIG. 1.

The infrared wavelength of the MicroLight 830 is specially selected to penetrate the epidermis, dermis and subcutaneous layers, entering the flexor tendons and surrounding tissues, as shown in FIG. 4. The wavelength range of the laser light is 800–870 nm and preferably 830 nm. By using a wavelength having such a range, the beam will not lose appreciable power when directed through a patient. Thus, using such a wavelength allows the device to probe deeply with a low power laser. In contrast, using a wavelength of greater than 900 nm., penetration will not be as deep and thus treatment will not be as effective. By the same token, using a wavelength lower than 800 nm. will result in deep penetrations but may be harmful to the tissues being irradiated.

Along its path, the laser deposits photons into the cells and nerve stimulation is immediate. Within minutes, microcirculation is improved bringing increased oxygen and blood flow to the problem area (e.g., a wrist). The beam also blocks pain enzymes and activates synthesis of endorphin enzymes.

The method of in the invention uses 830 nanometer (nm), 30 milliwatt (row) laser energy in the clinical management of a variety of acute and chronic soft tissue injury in performance animals. The LaserMedics laser tool is designed and calibrated to deliver approximately 1 Joule/ square centimeter per diode laser aperture. Therefore, the single diode laser delivers approximately 1 Joule/square centimeter during each operating period. This period is signaled by an audible beep coming from the battery end of the laser device. The operating period is 33 seconds and the operating power is 30 mw. Therefore, as mentioned above, this diode laser emits substantially 0.99 Joules during the operating period (30 mw×33 sec.=0.99 Joules per square centimeter).

The triple diode laser will also deliver approximately 1 Joule per diode in an approximate 3 centimeter (cm) circle and a maximum depth of approximately 5 cm. The arrangements of these diodes allow the operation to treat approximately 6 cm. of tissue area by simply rotating the laser device. The total dose of laser energy delivered is 1 Joule/ square centimeter over an approximately 6 centimeter area (e.g., with 2 duty cycles—a duty cycle includes a 60-degree rotation of the laser diode on its axis, as discussed in further detail below).

The maximum dose in any one location at any one treatment time is 4 Joules/sq cm. Doses higher than 4 J/sq cm. are to be fractionated during a 24-hour period.

The treatment area is determined by creating a 6 square centimeter grid over the affected area. The treatment area will extend 1.5 cm into the normal tissue (½ the diameter of the treatment head of the triple diode laser). Treatment will be administered by placing the head of the laser device in contact with shaved skin over the affected area. Alternatively, a clear laser transmission gel can be used over wounds and unshaven skin. The transmission gel should be copiously applied to the treatment area. The clear plastic cover should be placed over the head of the laser prior to placing the laser in contact with the patient's skin and/or the gel.

A typical treatment scenario includes determining a treatment grid area. A permanent marker could be used to delineate the grid made up of 6 square centimeters. This can be performed by measuring 5 cm. squares and dividing these squares into 4 parts (e.g., 5 cm×5 cm=25 $cm^2 \div 4 = \sim 6$ $cm^2$.) Thereafter, the affected skin area should be shaved and/or laser energy transmission gel should be applied over treatment grid.

Thereafter, the laser device is activated and held steady during the operating period. Then, the laser device is preferably rotated 60 degrees and the device is activated again. The laser device is moved to the next grid square and the above steps are repeated.

As discussed in more detail below, light produced by the device reduces the ability of lymphocytes to react to antigenic stimuli acting as an anti-inflammatory agent. Depending on the level of trauma, swelling (e.g., in the flexor tendons) begins to reduce in hours. As discussed in further detail below, if the situation in chronic, the inflamed area may require 2–3 treatments per week until there is a noticeable reduction in swelling and the flexor tendons glide freely (e.g., in the carpal tunnel) without compressing, for example, the median nerve.

Biologically, laser light produced by the device will increase the cell production rate in connective, tendinous and cartilaginous tissue. Additionally, laser light has the capability to increase the rate of regeneration of nerve cells, but will not stimulate bacterial growth.

The clinical effect of laser therapy depends on the amount of energy put into the tissues at each individual treatment point. Correct LLLT is a prerequisite of the desired clinical effect and within medical LLLT, a laser source having a mean power of 30–70 mW is preferably used.

To obtain optimum clinical effect, the tip of the laser probe must be in complete contact with the surface of the skin. The laser probe should preferably be kept at right angles to the surface of the skin. Otherwise, the light beam may be reflected off the surface resulting in less energy reaching the target. Contact over an irregular surface can be improved by using, for example, a suitable gel, which allows greater and more reliable contact of the device with the desired area. However, as discussed below in the specific treatment protocols, for the treatment of superficial ulcers direct contact is unnecessary and may be unpleasant for the patient.

Under practical, clinical conditions, the clinical effect is related to a maximum depth of treatment of 3–5 cm. However, if acupuncture points are used, the efficiency may be compared with acupuncture by means of needles, and the depth effect is the same.

With the correct dosage, laser light may penetrate several millimeters of bone. Consequently, specific LLLT of bone and bone marrow is not recommended, while problems affecting the periosteum can be treated. Preferably, a dosage of 0.5 to 10 Joules is used for each treatment point or from 16 seconds to 5 minutes, The present invention uses a unique combination of 33 seconds per point at a mean power of 30 mW. At a mean power of 30 mW, approx. 33 seconds of laser light should be used for establishing 1 J.

The biological effect of laser light includes cell growth stimulation (connective tissue, tendons, bone, muscles and nerves), cell regeneration (connective tissue, tendons, bone, muscles and nerves), revascularization (oedema inhibition, contraction loosening, anti-inflammatory, increase of microcirculation), anti-inflammatory (increases the microcirculation and reduces the ability of the lymphocytes to react to antigen stimuli, for all tissues), stimulation of nerve function (nerve tissue, increases the amplitude of the action potential, inhibition of clonus, acupuncture treatment), and reduction in the formation of fibrous tissue (following tissue damage the formation of fibrous tissue is reduced/retarded, e.g., after burns).

The clinical effect of laser light includes promotion of healing (as mentioned above revascularization/cell regeneration and cell growth stimulation, for all tissues), pain-relief (nerve tissue, tendons, periosteum, muscles and connective tissue).

To obtain the maximum clinical effect of LLLT, treatment should be performed on the correct points, with the correct distance between treatment points, with the correct dosage, with the correct interval between treatments, and as soon as possible after the onset of the problem, as discussed in further detail below.

Safety is an obvious concern when electromagnetic radiation is used to treat patients. There is no evidence of adverse events using LLLT in doses less than 4 Joules/$cm^2$ per treatment. Photothermal effects of extended dosage therapy in vitro on the skin and subcutaneous tissues in a rat model have been studied, in which extended doses of laser energy were evaluated having low incident power densities such as 830 nm infrared laser energy (60 mW, continuous wave, spot size 0.3 $cm^2$ power density=0.2 W/$cm^2$, irradiation times of 3 and 30 minutes, energy densities of 36 J/$cm^2$ and 360 J/$cm^2$, respectively) in vivo on rat skin and subcutaneous tissues. A group of identically handled but sham treated rats acted as controls. Macroscopically, there were no visible signs of alteration in skin color or texture. Histology revealed no difference in the epidermal, dermal, or subdermal tissue architecture in controlled, 3 minute or 30 minute irradiation groups. Thus, laser therapy within the above parameters is believed photothermally safe.

Cytogenetic effects have been evaluated in human leukocytes in vitro. Laser energy doses of 30–300 J/$cm^2$ produced dose-related cytostatic effects. Mitosis was inhibited completely when the dose exceeded 240 J/$cm^2$. There was a significant increase in the frequency of chromosome and chromatid breaks and gaps ($p<0.05$) and also an increase of sister chromatid exchange after 180 J/$cm^2$ ($p<0.05$). An increase in milosis occurred at lower doses (1 to 4 J/$cm^2$). However, this increase was not statistically significant at the $p<0.05$ level. These results indicate that LLLT is useful for stimulating cell proliferation in treatment sites and thereby contribute to the rate of wound repair and remodeling.

Various mechanisms of action have been proposed for the use of LLLT including energy supply, membrane stabilization, enhanced oxygen metabolism, altered calcium metabolism, altered sodium-potassium metabolism, immunocyte activation and induced cell division and migration into treated tissues. The addition of energy (i.e., heat) to tissues has been a therapy used since the advent of medicine. LLLT is another method for adding energy to tissues without the adverse effects of surface thermal energy.

The present inventor has found that the 830 nm wavelength has the unique property of being able to penetrate tissues up to 5 cm. in depth without causing superficial surface heat damage. Tissue exposure to laser energy has been shown to cause an increase in general metabolic activity. Recently, research has centered on oxygen metabolism and the effects of laser induced singlet oxygen and nitrous oxide on receptors and organelles in cells.

A wide range of LLLT effects is on calcium ion transport has been determined. Divalent calcium plays a crucial role in membrane function and stability and is also a critical second messenger in many forms of cell activity such as synthesis, secretion and intracellular communications. The sometimes varying treatment results obtained with lasers may be explainable by the patient's underlying and/or concurrent medical condition because such conditions can limit ability to respond to second messenger signals, including calcium and G-proteins.

The mechanism of pain attenuation is believed to involve the foregoing mechanisms occurring in nerve cells and nerve endings. Additionally, LLLT may decrease the volume of mitochondria in bradykinin affected cells. Bradykinin is one of the most potent pain-producing agents produced by the body and is responsible for dull, numbing pain of long duration. As rapid neuronal activity associated with a pain response consumes ATP, mitochondria usually expands with the increased demand for ATP. Following LLLT therapy, however, mitochondria decreases in size and blood flow increases and thus a decrease in bradykinin concentration could be caused by the increased blood flow and bradykinin production may be reduced due to an ATP shortage, thereby reducing pain.

Additionally, LLLT has been shown to cause mast cell degranulation in vivo. In recent studies, the tongues of Swiss mice irradiated with a single laser energy dose of 2.4 J showed vasodilatation and active mast cell degranulation in the tongue tissues. Following LLLT radiation, various substances, including histamine, heparin, and prostaglandin E2, were released. The release of histamine causes vasodilatation and may also be responsible for the removal of bradykinin and other chronic inflammatory substances from the local tissues.

The effect of LLLT on white blood cells has been examined in vitro. Exposure of cultured macrophages to LLLT has resulted in increased phagocytic activity. LLLT also affects calcium metabolism in macrophages resulting in activation of calcium dependent receptors. Macrophage activation can result in cytokine release which in turn results in site specific and condition specific responses, according to what tissue and what activity the macrophage is responding. These multifunctional effects on macrophages, neutrophils and mast cells may be synergistic to modify pain, edema, tissue repair and remodeling.

The mechanism of wound healing involves three mechanisms acting together. Tissue remodeling and regeneration is an energy intensive event and LLLT can supply energy to accelerate this event. LLLT in dentistry is useful for enhancing new bone formation and the rate of healing.

LLLT also has advantageous effects on collagen synthesis, metabolism, and the rate of defect closure and increased amounts of growth factors and cytokines may be produced by cells in LLLT treated wounds. LLLT is also useful in treating nerve paresthesia. Further, laser energy is useful in the interaction and its effect on fibroblasts and lymphocytes. Laser irradiation has a positive effect on the growth and replication of fibroblasts. Laser treated (1.5 J/cm$^2$) fibroblasts exhibit enhanced migration, locomotion, and differentiation characteristics.

The interaction of electromagnetic energy from exogenous sources is required for normal biological system function. Laser energy is also useful as an energy source and as an important signal to the organism to initiate tissue repair in acute and chronic conditions.

LLLT is classified according to the variations of power intensities from 1 mW to 500 mW, and has been employed successfully in the treatment of medical conditions ranging from pain attenuation to wound healing. If suitably applied, LLLT can accelerate the inflammatory phase of experimentally-induced wound healing. By altering cell membrane permeability, these therapies can modify cell behavior to stimulate tissue repair.

As mentioned above, LLLT exposure has been shown to affect the activity of at least three cell types involved in the production of granulation tissue during the proliferative phase of repair—macrophages, fibroblasts, and endothelial cells. It has been shown to increase permeability to calcium ions temporarily, a response which could act as an intracellular signal for some repair events. LLLT has been shown to stimulate the activity of cells operating in the wound healing process. For example, macrophages and mast cells can be prompted by LLLT to migrate towards a wound bed, alegranulate and release substances that accelerate repair. Different cell types may show variations in their response to different pulsing regimes and energy densities opening up the possibility of selective cell stimulation.

Alterations in calcium ion transport, activation of the immune system, and oxygen metabolism may explain the treatment effect in a large percentage of patients. Laser therapy is useful in the treatment of many musculoskeletal, inflammatory, and neurological conditions.

A variety of different areas can be treated. Examples of examination techniques used for obtaining probable treatment points are: 1) palpation of tender points (e.g., myositis); 2) visually perceived points (e.g., granulating ulcers); 3) radiologically verifiable points (e.g., fissure lines); and 4) acupuncture points (using a point seeker or acupuncture atlas).

For the treatment area, the total dosage preferably should not exceed 50 Joules for the first treatment because exceeding this range causes problems such as the top layer of all tissues may flake off. The point spacing is preferably 5 mm, 10 mm and 15 mm, consecutively, and depends on the indications and palpation findings. The point spacing is mentioned under the various treatment indications below.

A variety of different tissue structures can be treated to include skin, subcutaneous tissues and mucous membranes; muscles; tendons; the vascular system; the nervous system; periosteum; and joints. The indications for treatment include a variety of factors. For acute and chronic diseases, the treatment indicators include inflammation, necrosis/gangrene, contusions, oedema, haematomas, strains, sprains, avulsions, ruptures, dislocations, contractures, atrophy, paresis/paralysis, arthritis and postoperative patients.

The laser treatment techniques may vary according to the type of area to be treated and the condition thereof. The first technique is directly over the injury/from palpation of tender points. A second technique is indirectly/paravertebrally and includes trigger points, radicular pain areas, superficial nerve trunks, myofacial points, acupuncture points. A distance technique and contact technique is useful for wounds/ulcers, transplants and scar tissue. These techniques are performed by holding the tool near (but not on) the affected area.

Tests should be performed before and after laser treatment for palpation tenderness, mobility and muscle tone. The LLLT treatment duration and interval depends on the chronicity of the disease. Acute conditions and postoperative patients are usually treated every day or every second day until 4 treatments have been given. If it is necessary to continue therapy, treatment takes place 1–2 times a week for 1–2 weeks. Generally, treatment takes place until the symptoms have disappeared. For acute conditions, clinical improvement often takes place as a result of the reduction of pain. This effect can be noticed within 5 minutes of treatment and up to 2 hours at the latest (often before the patient leaves the clinic).

Chronic diseases are preferably treated twice during the first week and then 1–2 times a week during the next 4–8 weeks. The patient may feel more pain after the first treatment because treatment is accelerating the cell and having increased circulation through the affected area. However, this effect is only temporary. Generally, treatment continues after the symptoms have disappeared and takes place every 2nd–4th week until the palpation tenderness over the tender points has disappeared.

As mentioned above, the laser probe is typically applied at right angles to the treated area. To increase mobility, it may be necessary to treat "tight" muscles and tendons in the stretched position, which will require the patient to be treated at the limit of their pain tolerance. When treating joint lines, the joint is preferably slightly flexed so that it is "opened" as much as possible. The probe is applied using a firm contact with the skin overlying the joint surface.

Where no clinical effect is obtained, certain parameters should be considered and checked. For example, it should be determined whether the dosage is correct. It may be advantageous to increase dosage by 50% and the correct duration and interval of therapy should be checked as well as the correct treatment area and point spacing. Further, the selection of treatment points should be determined and verified, as well as whether there is sufficient contact between laser and contact surface.

Overdosing should be prevented. However, it is acknowledged that such a condition may occur. Clinically, overdosing produces an aggravation of the condition which can last from a few hours up to a few days (e.g., a temporary reaction which can be improved by discontinuing LLLT for 1–2 days, and afterwards dosage should be 25–50% lower than before). With chronic diseases this reaction, following the first LLLT treatment session, is not considered overdosing.

LLLT has no actual contraindications. However, the conditions of pregnant uterus, malignant melanoma and general malaise/fever, should be preferably avoided. Further, direct or indirect irradiation of the eyes should be avoided as the eye lens may concentrate the laser beam resulting in damage to the retina. Cancer tissue does not appear to be affected by LLLT.

The table shown in FIG. 5 illustrates general treatment dosages and is useful as a guide. The suggested dose should be adjusted according to the progress of the condition and the depth of penetration required.

FIG. 6 illustrates a Table listing conditions which respond to LLLT and for various tissue lesions with examples of individual types of tissue. In more details, the various tissue lesions responding to LLLT are described below along with specific treatment instructions.

Depending on the cause, LLLT is suitable for inflammation, although it is not the only form of therapy for bacterial infections. However, laser light has some antiviral effect (for instance in herpes). Using LLLT for inflammation can result in a spasmodic recurrence of the symptoms during the first phase of the treatment. The biological effect of laser light is the result of an increase in the microcirculation and a reduction of the ability of the lymphocytes to react to antigenic stimuli. All types of tissue with inflammatory changes can be treated to include dermatitis, gingivitis, myositis, tendinitis, tendovaginitis, tenovaginitis, bursitis, phlebitis, neuritis, periostitis, spondylitis, spondylosis, paraodontitis, paraodontosis, arthritis, arthrosis, fibrositis and contractures. Further, acne vulgaris, acne rosacea, subtrochanteric bursiris, fibrositis, trigger finger, and Dupuytren's contracture may be treated.

LLLT produces revascularization of tissues and pain relief. Therefore, LLLT should commence in the early stages of ischemia. LLLT also is especially recommended for ischemic, disuse or pressure atrophy. Similarly with other forms of atrophy, the prognosis depends on the cause, and it is advisable to start treatment at an early stage. Causal factors should be treated also. Atrophied tissues to include skin, muscles, subcutaneous tissue, nerves and mucosa, will also respond to treatment. The biological effect results from the stimulation of cell growth and tissue regeneration.

All types of tissue contusions can be treated with LLLT if treatment is started immediately after injury. However, some tendon contusions have a poor prognosis. The biological effect is due to the many effects of laser light: pain relief, revascularization, stimulation of cell growth, tissue regeneration, anti-inflammatory and the promotion of healing.

Haematomas (and other forms of oedema) will respond to LLLT with good effect. LLLT stimulates revascularization resulting in an increase of the microcirculation and resorption of the hematoma/oedema. This occurs after 2–4 days of therapy. To avoid a recurrence, treatment of the cause is necessary. LLLT also is suitable for all types of "overstretching" injuries such as muscles, tendons, nerves and joints and especially in the acute stage. The biological effect is primarily due to revascularization and the promotion of healing. LLLT can produce immediate pain relief and reduction of oedema, often eliminating the need for further medical treatment. LLLT is given for 1–4 days in conjunction with rest, ice, compression and elevation as necessary.

LLLT is advantageously used following the surgical repair of ruptures to promote healing and speedy recovery. All types of tissue can be treated, but tendon, ligament, and muscle ruptures are mainly seen in clinical practice. The biological effect of laser light can shorten the recovery period by 50%. LLLT for dislocated joints, either postoperatively or postmanipulatively, is similar to that for strains and sprains. The prognosis and the number of treatments required depends on the chronicity of the disease. Acute cases make an excellent recovery, especially if no joint structures are seriously injured. The biological effect is partly due to pain relief and reduction of oedema and partly due to revascularization and promotion of healing.

LLLT for contractures depends primarily on the cause as does the prognosis. Often it is necessary to continue the therapy over a long period (weeks/months). Indications for treatment include contractures of tendons/muscles and fibrous tissue formation (e.g., Dupuytren's contracture). The biological effect of laser light is due to pain relief, revascularization, stimulation of nerve function and the promotion of healing. LLLT significantly increases the healing of fractures and shorten the period of convalescence. When used for the treatment of fissures, LLLT reduces the healing time and relieves pain. The biological effect is due to revascularization and promotion of healing.

LLLT can also be used within cancer therapy and includes administration of a special drug which produces a cytotoxic effect when irradiated with a monochromatic light source.

SPECIFIC TREATMENT PROTOCOLS

Turning now to the specific treatment protocols briefly alluded to above, skin, subcutaneous tissue and mucous membranes can be effectively treated by LLLT.

For open wounds, the therapy involves LLLT, with dosage per point being preferably substantially 1 J/square cm. The number of points depends on the area, with the point spacing (e.g., the spacing between points of application) being preferably 1 cm into normal tissue around the wound. The treatment interval is preferably once a week for the first two weeks and then 2–3 times weekly. The total number of treatments is preferably to resolution or 45 days, whichever comes first.

For dermatitis, the therapy involves LLLT, with dosage per point being preferably substantially 0.5–1 J/square cm. The number of points depends on the area, with the point spacing being preferably every 6 square cm. The treatment interval is preferably daily or every other day. The total number of treatments is preferably 2–8. A temporary exacerbation of the symptoms is often seen after the first treatment because of increased circulation as described above.

For eczema, the therapy involves LLLT, with dosage per point being preferably substantially 0.5–1 J/square cm. The number of points depends on the area, with the point spacing being preferably every 6 square cm. The treatment interval is preferably every other day. LLLT for skin diseases may result in an increase of pain due to the pressure of the laser probe. However, treatment can be performed as distance laser treatment in which the convex lens is held 1–2 mm above the area of the skin affected. Contact can be increased by using a contact medium such as gel or a clear hydrogel.

For lack of healing/lack of granulation tissue formation, the therapy involves LLLT, with dosage per point being preferably substantially 0.5–2 J/square cm. The number of points depends on the area, with the point spacing being preferably every 6 square cm. The treatment interval is preferably daily for 5 days, then twice a week, if necessary. The total number of treatments is less than 4. Insufficient granulating wounds may require a longer treatment period.

For scar tissue contracture/exuberant granulation, the therapy involves LLLT, with dosage per point being preferably substantially 1.0–1.5 J/square cm. The number of points depends on the area, with the point spacing being preferably every 10–15 mm. The treatment interval is preferably every other day for the first week, then twice a week. The total number of treatments is less than 4. LLLT alone is not recommended for over-granulating tissue, but should be dosed postoperatively.

For fistulas, the therapy involves LLLT, with dosage per point being preferably substantially 2.0–4.0 J/square cm. depending on the depth of probing. The number of points is preferably one per fistula, with the point spacing being preferably one per fistula. The treatment interval is preferably daily. The total number of treatments is 4–6. When a foreign body is the cause, surgery is required. LLLT can be given postoperatively.

For edema/cysts/bursae, the therapy involves LLLT, with dosage per point being preferably substantially 1.0–2.0 J. The number of points depends on the area, with the point spacing being preferably every 6 square cm. The treatment interval is preferably daily. The total number of treatments for edema/bursae is 2–4 days. The effect of producing an increase in fluid drainage is due to the biological increase of the microcirculation by the laser energy. This effect is seen at an early stage of the treatment so that edema or a bursa may disappear within 2–4 days.

For disorders of muscles/acute conditions such as myositis/muscle contusions/muscle ruptures caused for example by inflammation/trauma, LLLT is used for anti-inflammatory, healing of tissues, and pain relief. The therapy involves LLLT, possibly postoperatively following the repair of muscle ruptures, with dosage per point being preferably substantially 2–4 J. The number of points depends on the area, with the point spacing (e.g., the spacing between points of application) being preferably 10–15 mm/depending on palpation findings. The treatment interval is preferably daily for the first 4 days then 2–3 times a week, if necessary. The total number of treatments for myositis would be 4–6 and 4–8 for muscle contusions. For myositis, an exacerbation of symptoms is often felt after the first 2–3 treatments. This condition is temporary, but if necessary the dosage should be decreased or treatment should be given every second day instead of every day.

For muscle atrophy/muscle contractures, the therapy involves LLLT, with the dosage per point substantially 4–7 J. The number of points depends on the area, with the point spacing being 1 cm. into normal tissue. The treatment interval is preferably 2–3 times a week, depending on the reaction pattern. The treatments should preferably be for 6 weeks and then maintenance treatments should be given, as required. The prognosis depends on causal circumstances which should be identified for each patient.

With regard to disorders of the nervous system, generally incomplete nerve lesions have a reasonably good prognosis. Complete lesions will require surgery and LLLT can be given postoperatively. LLLT for neural conditions produces pain relief, an increase of action potential, an increase of the microcirculation, and an increase in the regeneration of tissues.

For disorders of neuritis/neuralgia/neurotmesis, which are caused by inflammation/trauma, the dosage per point is substantially 1–2 J. The number of points depends on the extent of the problem, with the point spacing being every 5–10 nm. The treatment interval is preferably 1–2 times a week, depending on the reaction pattern and the total number of treatments is preferably 4–10. The benefits of such treatment are pain relief, anti-inflammatory, nerve regeneration and healing of tissue. LLLT often has an immediate pain relieving effect, and when considering ruptured nerves, LLLT is given postoperatively.

For contusions of nerves/neurectasis, caused, for example, by trauma, LELT is advantageous for pain relief, promotion of healing, and stimulation of nerve function. The dosage per point is preferably 2–4 J, with the number of points depending on the extent of the problem. The point spacing is preferably 5–10 mm and the treatment interval is preferably 2–3 times a week. The total number of treatments is preferably 1–4. Incomplete nerve lesions without tissue necrosis have a reasonable prognosis especially if treatment is commenced soon after injury.

For atrophy of nerves, caused, for example, by pressure, the benefits of LELT therapy include regeneration and revascularization. The dosage per point is preferably 3–5 J and the number of points depends on the extent of atrophy. The point spacing is preferably 10–15 mm and the treatment interval is 2–3 times a week, with the total number of treatments being weeks or months. The cause should be identified and corrected.

For paresis/paralysis, the benefit of LELT is stimulation of nerve function. LLLT is performed, possibly postoperatively, with the dosage per point being 1–4 J and the number of points depending on the extent of the problem. The point spacing is preferably 10–15 mm. with the treatment interval being daily for the first 4 days, then twice a week. The total number of treatments is from 4 days to 2 weeks (if effective, treatment can be continued over a long period, (possibly months). The cause should be identified and corrected.

For a prolapsed disc, the benefits include pain relief, cell regeneration, reduction of oedema, healing of tissues, and stimulation of acupuncture points result from LLLT (possibly postoperative LLLT) combined with other physiotherapeutic techniques, with the dosage per point being 1–4 J. The number of points depends on the extent of the problem. Lumbar disc lesions are treated bilaterally and symmetrically. Cervical disc lesions are treated in the midline and along the base of the skull. Point spacing is approximately 10–15 min. The treatment interval is daily for the first 4 days, then 2–3 times a week. The total number of treatments is, postoperatively, 4–6 days. With LLLT alone, it is 4–14 days (where there is an improvement, continue therapy). LLLT of the spinal cord in the lumbar region is hampered by the vertebrae, through which laser light does not penetrate. The secondary myogenic changes in the erector spinae are treated with 3–4 J per point.

Turning to disorders of the bone, for spondylitis/periostitis, the benefit of therapy is anti-inflammation. The therapy includes LLLT, possibly in conjunction with antibiotics, with the dosage per point being 3–4 J and the number of points depending on the area of treatment.

The point spacing is 10–15 mm/depending on the palpation findings and the treatment interval is 2–3 times a week. The total number of treatments is 4–8 initially (continue if improvement seen).

For spondylosis, the benefits of LLLT are pain relief, stimulation of nerve function and the therapy is LLLT, with a dosage per point of 3–4 J. The number of points depends on the area of treatment and the point spacing is 15 mm depending on palpation findings. The treatment interval is preferably twice a week and the total number of treatments is 2–4 weeks. Patients may remain symptom-free for up to 6 months but a recurrence should be expected. However, the interval between treatment sessions should be increased.

For fissures/fractures, the cause is typically trauma and inadequate nutrition. The benefits of therapy are healing of tissues, revascularization, pain relief. The therapy for fissures is LLLT, with wound dressing possibly being required. For fractures, postoperative LLLT is performed, with the dosage per point being 2–6 J and the number of points depending on the area of treatment. The point spacing is 15 mm and the treatment interval is daily for 4 days, then every third day thereafter. The total number of treatments is 4–10. LLLT reduces the recovery period and it can be used postoperatively following osteotomies. It is especially suitable in cases of non-union of fractures and pseudoarthroses (5–8 J).

Disorders of Joints

For arthritis, inflammation is normally the cause and the benefits of therapy are anti-inflammatory and pain relief. Therapy involves LLLT, possibly combined with drugs and other physiotherapeutic techniques. The dosage per point is 2–4 J and the number of points is 2–6 points depending on the size of the joint. The point spacing is 15 mm depending on the palpation findings and the amount of oedema. The treatment interval is 2–3 times a week, with the total number of treatments being as required. Inflammatory symptoms may be temporarily exacerbated after the first treatment.

For arthrosis, the benefits of therapy are anti-inflammatory, pain relief, revascularization and regeneration of synovial fluid. Therapy involves LLLT, possibly combined with other physiotherapy treatments. The dosage per point is 3–6 J depending on the size of the joint, with the number of points also depending on the size of the joint, palpation findings and mobility. Point spacing is variable and the treatment interval is 2–3 times a week, with the total number of treatments being 4–10. all arthroses do not necessarily respond to LLLT. If there is no effect after 4 treatments, dosage should be increased by 25–50%. If there is still no effect, then treatment with LLLT should be discontinued. The secondary myogenic and tendinous changes are the ones being treated.

For the condition of enchondrosis vertebralis, therapy should be LLLT similarly to that described above with regard to a prolapsed disc.

For strains and sprains caused by trauma, the benefits of therapy are pain relief, revascularization, reduction of oedema, and promotion of healing. Therapy involves LLLT, with the dosage per point being 2–4 J depending on the size of the joint, with the number of points also being 2 cm. between each point. The treatment interval is daily for 4 days, then every second/third day. The total number of treatments should be 4–8. Immediate relief of pain is often seen.

For dislocations caused by trauma, the benefits of therapy are pain relief, healing of tissues, revascularization and reduction of oedema. Therapy involves postmanipulative or postoperative LLLT, with the dosage per point being 4–6 J depending on the size of the joint, with the number of points being 2–6 depending on the size of the joint and the point spacing being 15 min. The treatment interval is daily for 4 days, then 2–3 times a week. The total number of treatments should be 4–10. Total or partial injury of joint-capsule and ligament, (including collateral ligaments and cruciate ligaments), is often seen. In cases of partial rupture, the effects of regeneration and revascularization by the LLLT is utilized by treatment directly over the insertion points of the ligaments.

For tendinitis, tendovaginitis, epondylitis and Achilles tendinitis caused by inflammation (often due to overloading of the tendon), the benefits of therapy are pain relief, anti-inflammatory, revascularization and reduction of oedema. Therapy involves LLLT and exercises, with the dosage per point being 1–4 J, with the number of points depending on the area being treated and the point spacing being 5–10 mm depending on palpation tenderness. The treatment interval is 2–3 times a week, with the total number of treatments being 2–4 days. Dosage is doubled after 2–3 treatments.

For tendon strains and contusions caused by trauma, the benefits of therapy are pain relief, healing of tissues, revascularization and reduction of oedema. Therapy involves LLLT, with the dosage per point being 2–4 J, with the number of points depending on the area being treated and the point spacing being 10–15 mm. The treatment interval is daily, with the total number of treatments being 4–10.

For tendon ruptures/following surgery caused by trauma, the benefits of therapy are reduction of the postoperative recovery phase and pain relief. Therapy involves postoperative LLLT, with the dosage per point being 2–4 J, with the number of points depending on the area being treated and the point spacing being 1–2 cm. depending on the lesion. The treatment interval is daily, with the total number of treatments being 4. In the inventor's experience, after postoperative LLLT, the healing phase can be reduced by 25–50%.

For bursitis, the therapy is similar to that above described in connection with diseases of the skin.

Disorders of the Vascular System

For hematoma/tissue infiltration after injection (e.g., diabetes) caused by trauma, the benefits of therapy are pain relief, revascularization, reduction and resorption of oedema. Therapy involves LLLT, with the dosage per point being 1–2 J, with the number of points depending on the area being treated and the point spacing being 10–20 mm. The treatment interval is daily, with the total number of treatments being 2–4. In the case of diabetes infiltration, the injection site should not be irradiated on the same day For phlebitis/lymphangitis/lymphadenitis caused by inflammation, the benefits of LLLT therapy are anti-inflammatory, pain relief and reduction of oedema, with the dosage per point being 1–2 J, the number of points depending on the extent of inflammation and the point spacing being 5–10 min. The treatment interval is daily, with the total number of treatments being 2–4.

Postoperative LLLT

LLLT has previously been described as suitable for postoperative therapy for pain relief, the promotion of tissue healing, reduction of oedema and to speed the recovery phase following surgery. Examinations have shown that postoperative LLLT (usually for 4 consecutive days) reduces the convalescence time by 25–50%. LLLT can be used after any surgical technique.

The benefits include pain relief, revascularization, promotion of healing, reduction of oedema and to speed the recovery phase. Therapy involves LLLT, with the dosage per point being 1–6 J depending on the tissue structures to be treated (see FIG. 5), with the number of points depending on the area to be treated and the point spacing being 5–15 mm. The treatment interval is daily, with the total number of treatments being 4. For orthopedic surgery, postoperative LLLT results in patient mobility at an earlier stage.

Recommended dosages for the first LLLT treatment are as described below. For acute conditions, 1–3 J per point should be used (e.g., Facet syndrome, "dead leg", conditions). Pain relief should be obtained and treatment can be conducted daily. For chronic conditions, 1–5 J per point should be used (e.g., for osteoporosis, epicondylitis). The reaction pattern should be observed and treatment can be twice a week.

For neurogenic conditions, 0.5–1 J per point should be used (e.g., for phantom pains, neuralgia). The reaction pattern should be observed and treatment can be conducted 1–2 times per week.

For oedema, 1 J per point with 2 cm. between each point should be used (e.g., for strains/sprains). Treatment can be conducted daily.

For wounds/ulcus cruris, 1 J per $cm^2$ can be employed. The surface of the wound should be measured and daily treatments should be performed at first with 1–2 J per point daily. Treatment can be performed postoperatively with 2–4 J per cm. For preliminary treatment of contractures/contractile tissue, 5–10 J per point is preferably employed, with daily treatment at first followed by stretching. Later, treatment can be performed 2–3 times per week.

The use of LLLT for conditions involving paresis and paralysis depends on the cause. The biological effect of the laser light depends on the stimulation of nerve fibers using acupuncture points. When used for cases of spastic paresis, at dosages of 5–10 J, LLLT reduces the tension in the tendon and therefore reduces contracture formation resulting in improved joint mobility. LLLT should be used in connection with general physiotherapy such as cold/hot packs, rehabilitation therapy, massage, traction, taping/plastering, frictions, manipulation, wound regime, and stretching.

As mentioned above, the purpose of laser treatment is pain relief, reduction of oedema, healing of tissues, reduction of inflammation resulting in an increase of mobility and, therefore, relevant rehabilitation therapy can be started more quickly if laser treatment is initiated as soon as possible after onset of the problem. Contrary to ultra-sound, for instance, laser treatment may be initiated immediately after trauma because laser light does not emit heat. Consequently, there will be no contraindications following alloplasty or after the insertion of other prostheses (metal etc.). Laser treatment is successfully applied in combination with other therapeutic treatments such as manual therapy, traction, stretchings, massage and also wound regimes. When laser treatment is performed, the therapist should always test for palpation tenderness, mobility and tone before and after the treatment.

The reaction depends on the condition which is treated. Acute conditions such as sports injuries, facet syndromes and strains usually show no reaction to the treatment. A response should be obtained e.g., pain relief; on palpation, by improved mobility or by reduction of oedema. Daily treatment of acute conditions is successful. Chronic conditions such as epicondylitis should be treated with a dosage high enough to produce a counterirritant reaction. The patient must be warned of this reaction as an exacerbation of symptoms may occur temporarily. This reaction is also seen when treating ulcus cruris. Chronic conditions should be treated 2–3 times a week depending on the reaction pattern.

For neurogenic conditions such as trigeminal neuralgia, phantom pains and sciatica, a strong reaction is often seen, and therefore the dosage should be reduced from the first treatment. At first, treatment takes place 1–2 times a week. A treatment reaction usually will occur within the first 24 hours and lessen during the next 24 hours. Treatment should not be repeated until the reaction from the first treatment has disappeared.

For the treatment of muscle injuries and wounds, improvement is due to an increase in the microcirculation within the cell structure resulting in an improved oxygen supply to the ischemic area. Daily treatment of contracted tissue such as Dupuytren's contracture is also successful at the beginning. Later, the treatment intervals should be increased. When fibrous tissue is treated, there is no treatment reaction but a softening of the tissues and a reduction of pain. This should be followed up by intensive stretching.

As described above, with the invention, a therapeutic method is provided in which laser therapy can reach deep into tissues and yet not harm the tissues, as in the conventional systems. More specifically, the inventive method involves selection and utilization of a non-thermal wavelength of between 800 nm. and 870, for a predetermined time period depending on the tissues to be treated, which can reach deep into tissues and yet will not have the destructive effect of high energy lasers. This powerful therapeutic effect is provided by the specific photodynamic properties inherent to low energy lasers and the inventive method utilizes a wavelength precisely within the light spectrum which has an optimum biological effect on the tissues combined with a lens system for maximum penetration, and utilizes precise and accurate dosimetry depending on the patient's area to be treated.

Thus, low level laser therapy (LLLT) (typically having a power intensity of less than 500 /mW/cm$^2$) is beneficial in medical, odontological and veterinary practices, and is advantageously used as an alternative or adjunctive therapy where other therapies are insufficient, or if the client requests treatment without the use of drugs, or as a supplementary therapy together with medication and, also to shorten the period of convalescence following surgery. LLLT is used within physical therapy and is a laser treatment at a level such that the localized temperature of the treated tissue does not exceed 36.5° C. While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A method of treating a patient having an external skin layer, comprising the following steps:

providing a laser source for emitting a laser light having a wavelength of between 800 nm and 870 nm;

diagnosing an afflicted area of said patient, a portion of said external skin layer being adjacent said afflicted area;

delivering said laser light to the afflicted area for at least one treatment cycle, said laser source being operable on said afflicted area at a level of 1 Joule/cm$^2$ per treatment cycle so as to therapeutically treat said afflicted area and such that said external skin layer is not destroyed;

monitoring said afflicted area after the treatment cycle has been completed; and repeating said steps of diagnosing and delivering said laser light to said afflicted area based on said monitoring step.

2. The method according to claim 1, wherein said wavelength of said laser light is preferably 830 nm.

3. The method according to claim 1, wherein said step of delivering said laser light includes delivering said laser light to a maximum depth of treatment of between 3 and 5 cm.

4. The method according to claim 1, wherein said step of delivering said laser light includes a step of contacting said afflicted area with said laser source.

5. The method according to claim 1, wherein said step of delivering said laser light includes a step of maintaining a predetermined distance between said laser source and said afflicted area.

6. A method of treating a patient, comprising the following steps:

providing a laser source for emitting a laser light having a wavelength of between 800 nm and 870 nm;

diagnosing an afflicted area of said patient;

delivering said laser light to the afflicted area for at least one treatment cycle, said laser source being operable on said afflicted area at a level of 1 Joule/cm$^2$ per treatment cycle;

monitoring said afflicted area after the treatment cycle has been completed; and repeating said steps of diagnosing and delivering said laser light to said afflicted area based on said monitoring step, wherein each treatment cycle of said at least one treatment cycle has a duration of 33 seconds.

7. A method of treating a patient, comprising the following steps:

providing a laser source for emitting a laser light having a wavelength of between 800 nm and 870 nm;

diagnosing an afflicted area of said patient;

delivering said laser light to the afflicted area for at least one treatment cycle, said laser source being operable on said afflicted area at a level of 1 Joule/cm$^2$ per treatment cycle;

monitoring said afflicted area after the treatment cycle has been completed; and repeating said steps of diagnosing and delivering said laser light to said afflicted area based on said monitoring step, wherein said laser light is homogeneous and continuous throughout said treatment cycle.

8. A method of treating a patient, comprising the following steps:

providing a laser source for emitting a laser light having a wavelength of between 800 nm and 870 nm;

diagnosing an afflicted area of said patient;

delivering said laser light to the afflicted area for at least one treatment cycle, said laser source being operable on said afflicted area at a level of 1 Joule/cm$^2$ per treatment cycle;

monitoring said afflicted area after the treatment cycle has been completed; and repeating said steps of diagnosing and delivering said laser light to said afflicted area based on said monitoring step, wherein said step of providing a laser source includes a step of providing a laser source having a mean power of between 30 mW and 70 mW.

9. A method of treating a patient with a laser light beam, comprising the following steps:

providing a laser source for emitting a laser light beam having a wavelength of between 800 nm and 870 nm;

diagnosing an afflicted area of said patient;

delivering said laser light beam to the afflicted area for at least one treatment cycle, said laser light beam irradiating said afflicted area at a level of 1 Joule/cm$^2$ per treatment cycle, said treatment cycle being for at least 33 seconds;

monitoring said afflicted area after the treatment cycle has been completed; and repeating said steps of diagnosing and delivering said laser light beam to said afflicted area based on said monitoring step.

10. The method according to claim 9, wherein said laser source has a wavelength of substantially 830 nm.

11. The method according to claim 9, wherein said step of providing a laser source includes a step of providing a laser source having a mean power of between 30 mW and 70 mW.

12. The method according to claim 9, wherein said step of delivering said laser light includes delivering said laser light to a maximum depth of treatment of between 3 and 5 cm.

13. The method according to claim 9, wherein said step of delivering said laser light includes a step of contacting said afflicted area with said laser source.

14. The method according to claim 9, wherein said step of delivering said laser light includes a step of maintaining a predetermined distance between said laser source and said afflicted area.

15. The method according to claim 9, wherein said step of delivering said laser light includes performing a grid treatment cycle comprising:

creating a grid over the affected area comprising squares measuring approximately 6 cm² each; and delivering said treatment cycle of said laser light to each of said squares, one square at a time.

16. The method according to claim 9, wherein said step of delivering said laser light includes performing a duty treatment cycle comprising:

delivering a treatment cycle of laser light at a first treatment angle;

rotating said laser source a predetermined angle from said first treatment angel; and delivering another treatment cycle of laser light, wherein the total energy supplied is at a level of 1 Joule/cm².

17. The method according to claim 9, wherein said monitoring step includes a step of restricting the total level of treatment to a level not greater than 4 J/cm² over a 24 hour period.

18. A method of treating a patient, comprising the following steps:

providing a laser source for emitting a laser light having a wavelength of between 800 nm and 870 nm;

diagnosing an afflicted area of said patient;

delivering said laser light to the afflicted area for at least one treatment cycle, said laser source being operable on said afflicted area at a level of 1 Joule/cm² per treatment cycle;

monitoring said afflicted area after the treatment cycle has been completed; and repeating said steps of diagnosing and delivering said laser light to said afflicted area based on said monitoring step, wherein said step of delivering said laser light includes performing a grid treatment cycle comprising:

creating a grid over the affected area comprising squares measuring approximately 6 cm² each; and delivering said treatment cycle of said laser light to each of said squares, one square at a time.

19. A method of treating a patient, comprising the following steps:

providing a laser source for emitting a laser light having a wavelength of between 800 nm and 870 nm;

diagnosing an afflicted area of said patient;

delivering said laser light to the afflicted area for at least one treatment cycle. said laser source being operable on said afflicted area at a level of 1 Joule/cm² per treatment cycle;

monitoring said afflicted area after the treatment cycle has been completed; and repeating said steps of diagnosing and delivering said laser light to said afflicted area based on said monitoring step, wherein said step of delivering said laser light includes performing a duty treatment cycle comprising:

delivering said treatment cycle of laser light at a first treatment angle;

rotating said laser source a predetermined angle from said first treatment angle; and delivering another said treatment cycle of laser light, wherein a total energy supplied is at a level of 1 Joule/cm².

20. A method of treating a patient, comprising the following steps:

providing a laser source for emitting a laser light having a wavelength of between 800 nm and 870 nm:

diagnosing an afflicted area of said patient:

delivering said laser light to the afflicted area for at least one treatment cycle, said laser source being operable on said afflicted area at a level of 1 Joule/cm² per treatment cycle:

monitoring said afflicted area after the treatment cycle has been completed: and repeating said steps of diagnosing and delivering said laser light to said afflicted area based on said monitoring step, wherein said monitoring step includes a step of restricting the total level of treatment to a level not greater than 4 J/cm² over a 24–hour period.

* * * * *